(12) United States Patent
Mizutani et al.

(10) Patent No.: US 7,727,209 B2
(45) Date of Patent: Jun. 1, 2010

(54) INTERLABIAL PAD AND INDIVIDUAL PACKAGING BODY FOR INDIVIDUAL PACKAGE OF INTERLABIAL PAD

(75) Inventors: Satoshi Mizutani, Kagawa (JP); Yuki Noda, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 246 days.

(21) Appl. No.: 10/782,385

(22) Filed: Feb. 18, 2004

(65) Prior Publication Data

US 2004/0193124 A1 Sep. 30, 2004

(30) Foreign Application Priority Data

Feb. 18, 2003 (JP) .............................. 2003-040368

(51) Int. Cl.
*A61F 13/15* (2006.01)
*A61F 13/20* (2006.01)

(52) U.S. Cl. .................... 604/385.17; 604/385.01; 604/385.02

(58) Field of Classification Search ................ 604/354, 604/364, 385.02, 385.11, 385.13, 385.17, 604/386, 387; 206/438, 440
See application file for complete search history.

(56) References Cited

U.S. PATENT DOCUMENTS

| 3,510,587 | A |   | 5/1970  | Marder et al. |          |
|-----------|---|---|---------|---------------|----------|
| 3,575,173 | A | * | 4/1971  | Loyer         | 604/364  |
| 3,606,887 | A |   | 9/1971  | Roeder        |          |
| 3,665,923 | A | * | 5/1972  | Champaigne, Jr. | 604/364 |
| 3,683,919 | A | * | 8/1972  | Ells          | 604/364  |
| 4,333,464 | A | * | 6/1982  | Nakano        | 604/364  |
| 4,595,392 | A | * | 6/1986  | Johnson et al. | 604/385.17 |
| 5,026,363 | A | * | 6/1991  | Pratt         | 604/385.21 |
| 5,300,358 | A | * | 4/1994  | Evers         | 442/396  |
| 5,557,809 | A | * | 9/1996  | Adams         | 4/245.3  |
| 5,681,299 | A | * | 10/1997 | Brown         | 604/364  |
| 5,885,265 | A | * | 3/1999  | Osborn et al. | 604/367  |

(Continued)

FOREIGN PATENT DOCUMENTS

CN 1235534 A 11/1999

(Continued)

OTHER PUBLICATIONS

Search Report for WO 2004/075802 A1, Mizutani et al., Sep. 2004, WIPO.*

(Continued)

*Primary Examiner*—Michele Kidwell
(74) *Attorney, Agent, or Firm*—Morrison & Foerster LLP

(57) ABSTRACT

An interlabial pad, which can be discarded by flushing down a toilet and yet with which neither the functions and comfort during use of the interlabial nor the functions of a septic tank are damaged, is provided. The interlabial pad comprises: an absorbent body absorbing liquids; and a cover body covering the absorbent body in an enclosing manner and comprising a liquid permeable surface side sheet and a liquid impermeable back face side sheet. The cover body is arranged from a plurality of small sheet pieces and the small sheet pieces that are adjacent each other are mutually overlapped and form seam parts. The seam parts are set so as to become weakened in physicochemical strength upon permeation of water and separate into the plurality of small sheet pieces when the interlabial pad is discarded by being flushed down a toilet.

12 Claims, 8 Drawing Sheets

U.S. PATENT DOCUMENTS

| | | | |
|---|---|---|---|
| 6,258,074 B1 * | 7/2001 | Prazak | 604/385.17 |
| 6,802,833 B2 * | 10/2004 | Kudo | 604/385.02 |
| 6,929,628 B2 * | 8/2005 | George | 604/385.11 |
| 2001/0051796 A1 * | 12/2001 | Noda et al. | 604/383 |
| 2002/0042599 A1 | 4/2002 | Zhao | |
| 2002/0177827 A1 | 11/2002 | Noda et al. | |
| 2003/0105440 A1 * | 6/2003 | Kurata et al. | 604/364 |
| 2004/0073184 A1 * | 4/2004 | Ohba | 604/385.17 |
| 2004/0122399 A1 * | 6/2004 | McDaniel | 604/385.02 |
| 2004/0158222 A1 * | 8/2004 | Mizutani et al. | 604/385.17 |

FOREIGN PATENT DOCUMENTS

| | | | |
|---|---|---|---|
| CN | 1279597 A | | 1/2001 |
| DE | 1766437 B1 | | 3/1972 |
| EP | 0 888 764 A1 | * | 1/1999 |
| GB | 1334078 A | | 10/1973 |
| JP | 40-6954 | | 3/1965 |
| JP | 40-36397 | | 12/1965 |
| JP | 7-136206 A | * | 5/1995 |
| JP | 07-136209 A | | 5/1995 |
| JP | 9-132814 A1 | | 5/1997 |
| JP | 10-243962 A | | 9/1998 |
| JP | 2000-501322 A1 | | 2/2000 |
| JP | 2001-79037 A1 | | 3/2001 |
| JP | 2001-145669 A1 | | 5/2001 |
| JP | 2001-190590 A1 | | 7/2001 |
| JP | 2001-190596 A1 | | 7/2001 |
| JP | 2001-190597 A1 | | 7/2001 |
| JP | 2001-198160 A1 | | 7/2001 |
| JP | 2001-204761 A1 | | 7/2001 |
| JP | 2001-231816 A1 | | 8/2001 |
| JP | 2001-523520 A | | 11/2001 |
| JP | 2001-523521 A | | 11/2001 |
| JP | 2001-523523 A | | 11/2001 |
| JP | 2002-78733 A1 | | 3/2002 |
| JP | 2002-102280 A1 | | 4/2002 |
| JP | 2002-263137 A1 | | 9/2002 |
| WO | WO-98/08475 A1 | | 3/1998 |
| WO | WO-98/29078 A1 | | 7/1998 |
| WO | WO-99/00083 A1 | | 1/1999 |
| WO | WO-99/26573 A1 | | 6/1999 |
| WO | WO 99/26573 A1 | * | 6/1999 |
| WO | WO-99/26574 A1 | | 6/1999 |
| WO | WO-99/26577 A1 | | 6/1999 |
| WO | WO-01/66160 A1 | | 9/2001 |
| WO | WO-02/13877 A2 | | 2/2002 |
| WO | 02/094159 A1 | | 11/2002 |
| WO | WO-02/094146 A1 | | 11/2002 |
| WO | WO-02/094148 A1 | | 11/2002 |

OTHER PUBLICATIONS

Patent application JP 2001-392521, provided by WIPO/PATENTSCOPE.*

Merriam-Webster Online, definition of "piece"; www/.merriam-webster.com/dictionary/piece.*

Patent application JP 2001-392521, provided by WIPO/PATENTSCOPE, 2002.*

Merriam-Webster Online, definition of "piece"; www/.merriam-webster.com/dictionary/piece, 2008.*

International Search Report for PCT/JP2004/001727 mailed Mar. 23, 2004.

* cited by examiner

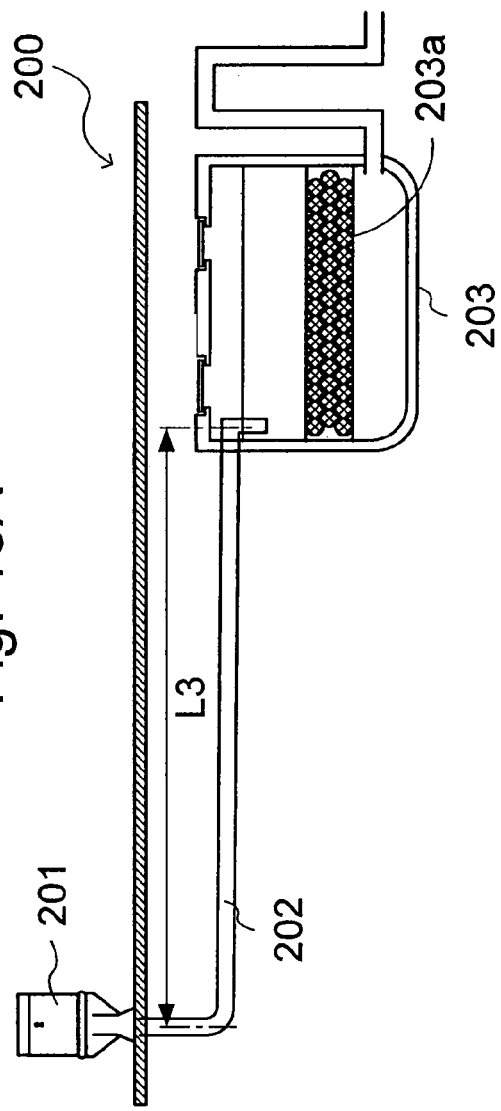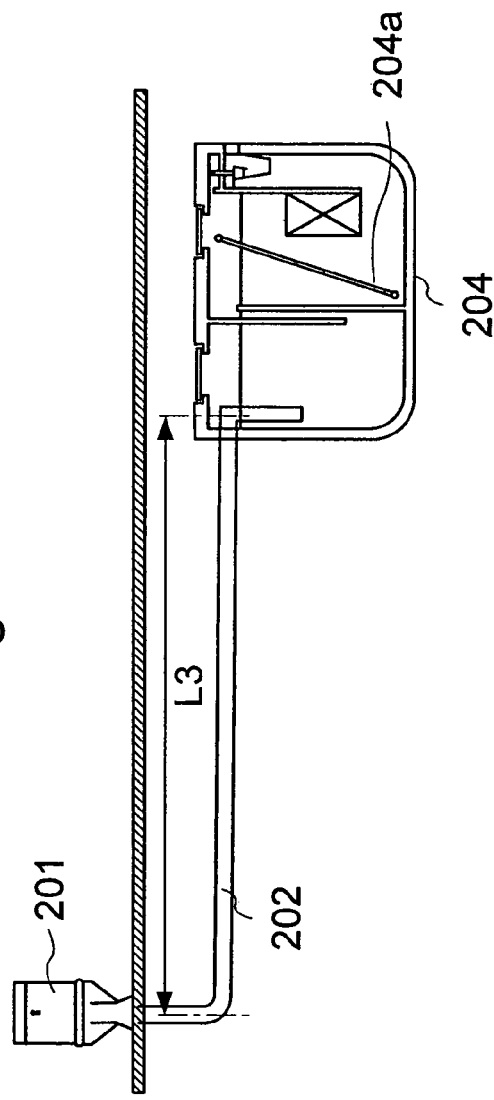

INTERLABIAL PAD AND INDIVIDUAL PACKAGING BODY FOR INDIVIDUAL PACKAGE OF INTERLABIAL PAD

FIELD OF THE INVENTION

The present invention relates to an interlabial pad to be fitted between a woman's labia. To be more specific, the present invention relates to an interlabial pad that can be discarded in a toilet and an individual packaging body for individual package of an interlabial pad.

DESCRIPTION OF RELATED ART

Interlabial pads, which are fitted between a woman's labia and absorb menstrual blood, urine, and other body fluids, have been known as absorbent articles for menstruation or for prevention of continence or for both of these purposes. As such an interlabial pad, an interlabial pad, which comprises a surface side sheet, a back face side sheet, and an absorbent body, disposed between the surface side sheet and the back face side sheet and absorbing and holding body fluids, and with which the back face side sheet is equipped with a mini-sheet piece for insertion of the pad using fingers, has been proposed (for example, International Patent Publication Pamphlet No. 02/094148).

Also in order to facilitate the discarding of an interlabial pad after use, an interlabial pad has been proposed with which the back face sheet of the interlabial pad is arranged as a biodegradable sheet or a water disintegrable sheet. For example, a biodegradable sheet, mainly formed of polybutylene succinate, is used for the back face side sheet of an interlabial pad (trade name: Envive (Moderate)) that has been test-sold in the USA by The Procter and Gamble Corp. (referred to hereinafter as "PG Corp."). This sheet has a size with a length dimension of 90 mm and a width dimension of 50 mm and the shape of the sheet is elliptical.

When a biodegradable sheet is used as the back face side sheet as in this product, since the interlabial pad is subject to biodegradation after use, the used interlabial pad can be disposed by flushing down a toilet, and yet even if the interlabial pad is put in a highly wetted state by the body fluids of a user, the leakage of the body fluids from the interlabial pad can be prevented.

However, when a biodegradable sheet is flushed down a toilet, since it does not disintegrate and become dispersed readily, it may clog a septic tank. For example, it was confirmed that when the abovementioned Envive (Moderate) is discarded in a device simulating a toilet with a small-scale combined treatment septic tank or an independent treatment septic tank, the product becomes retained on the filter element of the small-scale combined treatment septic tank or the aeration tube of the independent treatment septic tank and is thus high in the danger of obstructing the functions of the septic tank.

On the other hand, when a water disintegrable sheet, having polyvinyl alcohol, etc. as the raw material, is used as the back face side sheet, the back face side sheet will dissolve or swell and disperse upon coming into contact with the water in the toilet bowl, in the pipe, and in the septic tank. However, it is extremely difficult to prevent the problem of leakage, etc. during use of the interlabial pad and yet enable the water disintegrable sheet to dissolve or swell and become dispersed readily in water. For example, when for the purpose of slowing down the rates of dissolution and disintegration of the water disintegrable sheet and preventing the leakage of body fluids during use of the interlabial pad, the polymerization degree and saponification degree of the water disintegrable polymer are increased, the membrane thickness is increased, or an additive is mixed, etc., the rigid sensation of the water disintegrable sheet is increased as well. In this case not only will a user be subject to discomfort but since the dissolution and disintegration rates of the water disintegrable sheet are also decreased, the retention time in the filter element or aeration tube of the septic tank will be long. Also, depending on the type of additive, the microbial activity in the septic tank may be affected.

It was thus difficult with the prior art to enable an interlabial pad to be discarded after use by flushing it down a toilet without damaging the functions of a septic tank and yet prevent the leakage of body fluids and the lowering of the comfort of use.

SUMMARY OF THE INVENTION

The present invention has been made in view of such issues as the above and an object thereof is to provide an interlabial pad, which can be discarded by flushing down a toilet without damaging the functions of a septic tank and yet which is not lowered in the functions and comfort during fitting of the interlabial pad. That is, the present invention provides an interlabial pad, with which after the interlabial pad is discarded after use by flushing down a toilet, a cover body, covering an absorbent body, or in particular, a back face side sheet, which is a part of the cover body, separates into a plurality of small sheet pieces and becomes dispersed in water so that in the wetted state during use, the interlabial pad prevents the leakage of menstrual blood without disintegrating and is maintained in a good state of use.

Specifically, the present invention provides an interlabial pad and a packaging body for individual package of interlabial pad, such as the following.

(1) An interlabial pad comprising: an absorbent body for absorbing liquid; and a cover body covering the absorbent body in an enclosing manner and comprising a surface side sheet having a permeable property for liquid and a back face side sheet having an impermeable property against liquid; the interlabial pad being fitted between labia with the surface side sheet set at a body side; wherein the cover body is provided with a continuous or discontinuous parting zone that is parted by actions of water, along which the cover body is separated into a plurality of small sheet pieces when water acts.

The parting zone is a part that is set to be weakened in physicochemical strength when it is permeated with water. The parting zone is formed, for example, by adhering a plurality of small sheet pieces using a water disintegrable adhesive agent or providing a sheet with a plurality of perforation-like slits so that the parting zone disintegrates and disperses into some sheet pieces by water pressure or flow, etc.

Here, "water disintegrability" refers to the property of disintegrating readily by the actions of water. Also, "actions of water" refers to the action caused by water permeating into a certain object and changing the physicochemical characteristics of that object, including the physical action caused by water flow. With the present invention, in order to disperse the cover body into small pieces, it is preferable that the cover body is exposed to water so that water permeates into the cover body, and is moved underwater.

With the present invention, the cover body of the interlabial pad that has been discarded in a toilet after use is disintegrated at the parting zone and dispersed into small pieces by the actions of water. The interlabial pad will therefore not be retained in a filter element or an aeration tube of a septic tank and the possibility of damaging the functions of the septic tank can thus be reduced.

(2) The interlabial pad according to (1); wherein the parting zone is provided in the back face side sheet.

Though there are no restrictions regarding the position at which the parting zone is provided as long as the position is such that the leakage of the body fluids held by the absorbent body can be prevented, the parting zone is preferably provided in the back face side sheet as in the invention described in (2). When a parting zone is provided in the surface side sheet, the fitting comfort may become lowered since the surface side sheet comes in contact with the labia.

(3) The interlabial pad according to (1) or (2); wherein the parting zone is a seam part formed by overlapping the plurality of small sheet pieces one another.

With the present invention, the cover body is formed of a plurality of small sheet pieces that are smaller than the main interlabial pad body, and seam part is provided as a parting zone at a portion at which the small sheet pieces are mutually overlapped. Thus when the interlabial pad is discarded in a toilet, water permeates into the interlabial pad to cause the physicochemical strength of the seam parts to weaken and the cover body disperses in water in the form of the plurality of small sheet pieces, thereby enabling reduction of the danger of damaging the functions of a septic tank.

(4) The interlabial pad according to (3); wherein the plurality of small sheet pieces are adhered together at the seam part by an adhesive agent.

With the present invention, the plurality of small sheet pieces that overlap at the seam part are adhered together and the airtightness between these small sheet pieces is thereby increased. Body fluids will thus be less likely to enter between the small sheet pieces during use of the interlabial pad and the leakage of body fluids can thus be prevented. Also, a water disintegrable adhesive agent is applied between the small sheets that are mutually overlapped and the body fluids do not come in contact with the water disintegrable adhesive agent during use of the interlabial pad. Separation into the plurality of small sheet pieces that make up the cover body can thus be prevented during use of the inrterlabial pad.

(5) The interlabial pad according to (3) or (4); wherein the seam part is a longitudinal seam part extending in a longitudinal direction of the interlabial pad; and a sheet piece which overlaps the other sheet piece at the longitudinal seam part and covers a side closer to a longitudinal central line of the interlabial pad is positioned at the absorbent body side.

The present invention's interlabial pad is fitted between labia after being folded in two along the longitudinal central line. Body fluids that are excreted from the labia thus flow from the vicinity of the center of interlabial pad towards the outer edges. Here, in the invention according to (5), two small sheets that overlap at a seam part overlap in a manner such that the small sheet piece that is closer to the longitudinal central line is positioned at the inner side of the interlabial pad and the small sheet piece that is closer to the outer edge is positioned at the outer side of the interlabial pad. Body fluids that flow from the center to the outer edges of the interlabial pad can thus be prevented from entering into the parts at which the small sheet pieces overlap with each other and leakage of body fluids can thus be prevented.

Also with the present invention, since the seam part is long in length, a large amount of water enters into the seam parts and between the respective small sheet pieces from various directions when the interlabial pad is discarded into a toilet after use, the cover body is readily separated into the plurality of small sheet pieces.

(6) The interlabial pad according to (3) or (4); wherein the seam part is a lateral seam part extending in a lateral direction of the interlabial pad; and a sheet piece which overlaps the other sheet piece at the lateral seam part and covers a side that becomes a dorsal side when the interlabial pad is fitted between labia is positioned at the absorbent body side.

With the present invention, the small sheet pieces are overlapped so that the small sheet pieces, which cover the side closer to the dorsal side when the interlabial pad is fitted on, are positioned at the inner side of the interlabial pad. Body fluids, flowing along the interlabial pad in the direction from the ostium vaginae towards the ventral side can thus be prevented from entering into the seam part at which the small sheet pieces overlap with each other and leakage of body fluids can thus be prevented.

(7) The interlabial pad according to any one of (3) to (5); wherein the seam parts contain a longitudinal seam part extending in the longitudinal direction of the interlabial pad and a lateral seam part extending in the lateral direction of the interlabial pad; and a sheet piece which overlaps the other sheet piece at the longitudinal seam part and covers a side closer to a longitudinal central line of the interlabial pad is positioned at the absorbent body side; and a sheet piece which overlaps the other sheet piece at the lateral seam part and covers a side that becomes a dorsal side when the interlabial pad is fitted between labia is positioned at the absorbent body side.

With the present invention, since the cover body consists of at least four small sheet pieces, when the interlabial pad is discarded in a toilet after use, it disperses into these small sheet pieces, thereby preventing the damaging of the functions of a septic tank. Also, body fluids that flow from the center of the interlabial pad to the outer edges are prevented from entering into the parts at which the small sheet pieces are mutually overlapped and the leakage of the body fluids can thus be prevented.

(8) The interlabial pad according to any one of (1) to (7); wherein the back face side sheet is equipped with a mini-sheet piece on a surface at a side opposite to the absorbent body side.

With the present invention, since in the process of fitting the interlabial pad between the labia, a finger can be inserted between the back face side sheet and the mini-sheet piece and the labia can be spread apart by the fingers, the interlabial pad can be fitted securely up to the vestibular floor. The forming of a gap between the interlabial pad and the vestibular floor or the labial inner walls can thus be prevented.

In the case where the back face side sheet is provided with lateral seam part and this back face side sheet is equipped with a mini-sheet piece, one of the small sheet pieces that overlap at the lateral seam part, which covers the side that becomes the dorsal side when the interlabial pad is fitted between labia, is positioned at the absorbent body side. Furthermore, the mini-sheet piece is adhered onto the back face side sheet so as to have an opening opened toward the ventral side. By this arrangement, when in the process of fitting on the interlabial pad, a finger is inserted between the back face side sheet and mini-sheet piece from the direction that is to become the ventral side, the finger can be prevented from becoming erroneously inserted into a lateral seam part and thereby damaging this seam part.

(9) The interlabial pad according to any one of (2) to (8), wherein the back face side sheet is made uneven at least at the surface opposite to the absorbent body side.

With the present invention, when the interlabial pad is discarded into a toilet, the interlabial pad, which was folded in two during use, will open up readily in water due to the unevenness of the back face side sheet. The seam part of the back face side sheet is thereby exposed to water and the back face side sheet disperses readily into the plurality of small sheet pieces.

Furthermore according to the present invention, the frictional resistance, which arises due to the contacting of the back face side sheet with itself during use of the interlabial pad, is lowered and the back face side sheet is made less likely to become adhered to itself in the wetted state. The back face side sheet can therefore match the movements of a user without becoming entwined with itself and the labial inner walls and the interlabial pad can be kept in a state of good, close contact.

(10) A packaging body for individual package of interlabial pad, comprising: a packaging sheet; and an interlabial pad covered by the packaging sheet; wherein the packaging sheet is provided with a continuous or discontinuous parting zone that is parted by actions of water, along which the packaging sheet is separated into a plurality of small sheet pieces when water acts.

With the present invention, when the packaging body is discarded into a toilet, a large amount of water enters between the respective small sheet pieces from various directions. The packaging sheet that makes up the packaging body therefore does not retain its original form and becomes disintegrated and dispersed into the plurality of small sheet pieces, thereby enabling prevention of the damaging of a septic tank.

(11) The packaging body for individual package of interlabial pad according to (10); wherein the packaging sheet is a liquid impermeable sheet with an impermeable property against liquid.

With the present invention, the entry of water from the exterior can be blocked without fail. Thus even if water is splashed onto the packaging body for individual package or the packaging body is dropped onto a toilet floor by mistake, the interlabial pad inside the packaging body for individual package will not become wetted or soiled, thus providing excellent sanitation.

BRIEF DESCRIPTION OF THE DRAWINGS

FIG. 13A is a schematic view of a simulated night soil treatment device having a small-scale combined treatment septic tank.

FIG. 13B is a schematic view of a simulated night soil treatment device having an independent treatment septic tank.

DETAILED DESCRIPTION OF THE INVENTION

Interlabial pads according to the present invention shall now be described with reference to the drawings. In the description that follows, members that are the same shall be provided with the same symbols and description thereof shall be omitted or simplified.

Figure 1A:
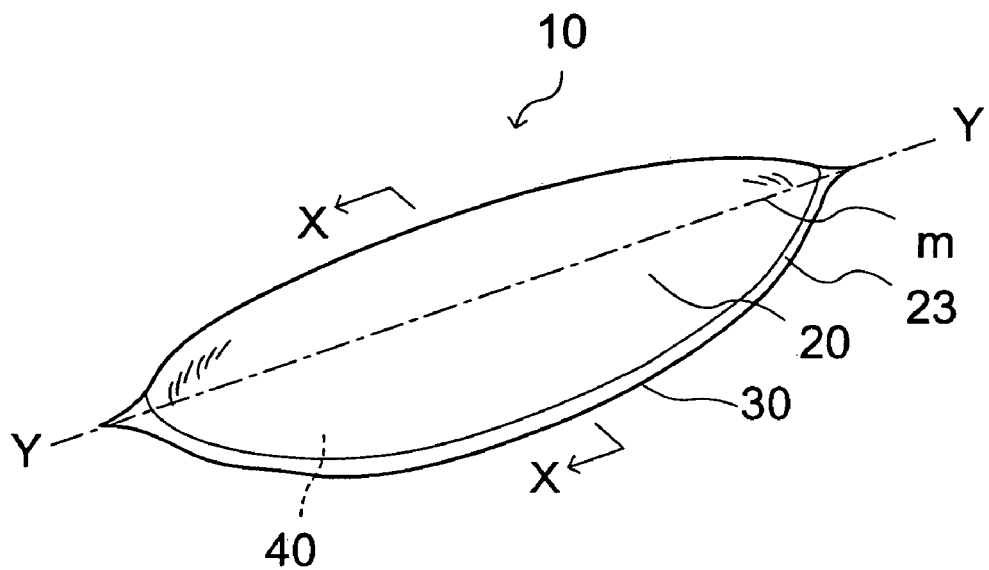
FIG. 1A is a perspective view of an interlabial pad of a first embodiment of the present invention.
Figure 1B:
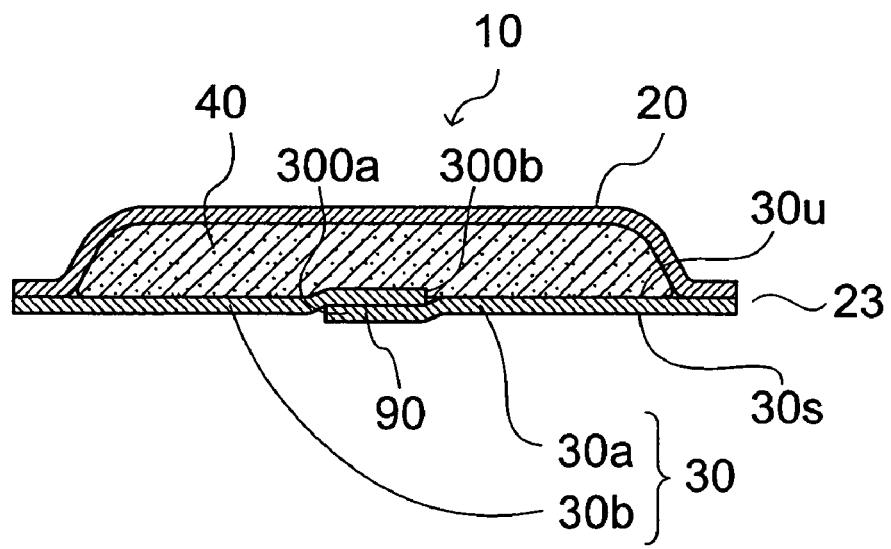
FIG. 1B is a sectional view along line X-X of the interlabial pad of FIG. 1A.
Figure 2:
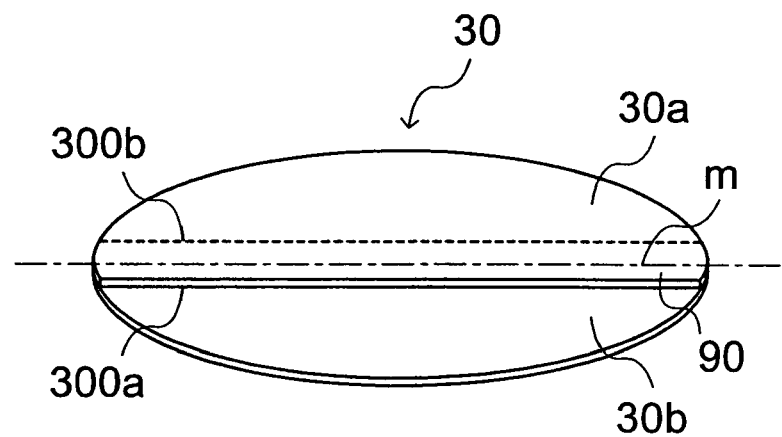
FIG. 2 is a perspective view of a back face side sheet used in the interlabial pad of the first embodiment.
Figure 3:
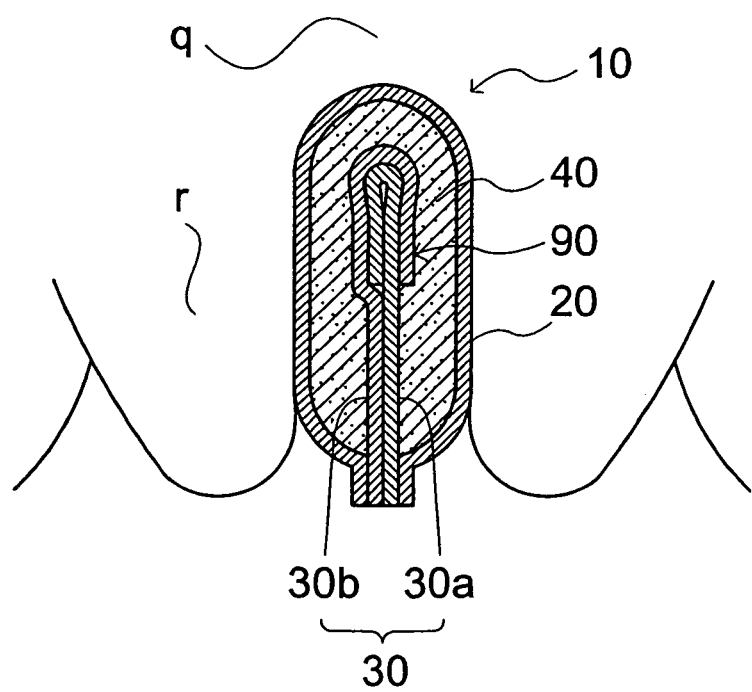
FIG. 3 is a diagram showing a state in which the interlabial pad of the first embodiment is fitted between labia.

FIG. 1A and FIG. 2A show diagrams of an interlabial pad 10 of a first embodiment of the present invention, with FIG. 1A being a perspective view of interlabial pad 10 and FIG. 1B being a sectional view along line X-X, in other words, along the lateral of interlabial pad 10. FIG. 2 is a perspective view showing a back face side sheet 10 of interlabial pad 10. FIG. 3 is a diagram showing the state in which interlabial pad 10 is fitted between labia.

As shown in FIG. 1A and FIG. 1B, an interlabial pad 10 has an absorbent body 40, which absorbs body fluids and other liquids, and the absorbent body 40 is covered by a cover body 23. The cover body 23 is provided with a surface side sheet 20, having a permeable property for liquids which allows the permeation of liquids, including menstrual blood, urine, and other body fluids (hereinafter, this property shall be referred to as "liquid permeability"), and a back face side sheet 30, having an impermeable property against liquids which does not allow the permeation of liquids (hereinafter, this property shall be referred to as "liquid impermeability"). The absorbent body 40 is disposed between the surface side sheet 20 and the back face side sheet 30.

For use, the interlabial pad 10 is folded in two along a longitudinal central line m so that the back face side sheet 30 is set at an inner side and the surface side sheet 20 is set at an outer side. Upon being folded in this manner, the interlabial pad 10 is fitted, as shown in FIG. 3, so that the surface side sheet 20 becomes a body side that contacts the body and the folded part contacts vestibular floor q of labia r. Since with the interlabial pad 10, which has thus been fitted between the labia, the surface side sheet 20 is liquid permeable, body fluids that flow down the labial inner walls permeate through the surface side sheet 20 and become absorbed and held by the absorbent body 40. Since the back face side sheet 30 of the interlabial pad 10 is liquid impermeable, the body fluid held by the absorbent body 40 is retained in the absorbent body 40 without leaking out to the exterior of the interlabial pad 10.

The interlabial pad 10 is long in the longitudinal direction indicated by line Y-Y, short in the lateral direction indicated by line X-X, and has a substantially elliptical shape in plan view. The size of the interlabial pad 10 in the longitudinal direction is in the range of 40 to 180 mm and preferably 70 to 130 mm. If the length is less than 40 mm, depending on the individual differences among users, it may not be possible to cover the entirety of the vestibular floor in the longitudinal direction, which extends from the ventral side to the dorsal side, and leakage of body fluids may occur. On the other hand, a length greater than 180 mm is unfavorable since the region that protrudes outside from the labia will be too big and readily contact vulvar parts, etc. and increase the possibility for interlabial pad 10 to fall off from the labia.

The size of interlabial pad 10 in the lateral direction is in the range of 25 to 100 mm and preferably 40 to 80 mm. If the width is less than 25 mm, depending on the individual differences among users, it may not be possible to cover the entirety of the inner labial walls and leakage of body fluids may occur. On the other hand, a width greater than 100 mm is unfavorable since the region that protrudes outside from the inner labial walls will be too great and readily contact vulvar parts, etc. and increase the possibility for interlabial pad 10 to fall off from the labia.

Though the shape of interlabial pad 10 is a substantially elliptical shape in the plan view of the present embodiment, the shape is not limited to this as long as the form is such that the pad can be fitted and held between the labia. Other forms of the overall shape of the interlabial pad 10 include, for example, rectangular shapes, gourd-like shapes, teardrop shapes, etc. Also, though the interlabial pad 10 of the present embodiment is substantially planar, the cross-sectional shape in the lateral direction may be folded three-dimensionally into a substantially V-like shape.

The surface side sheet 20 and the back side sheet 30 are joined at least partially at the peripheral edge parts of the absorbing member 40 and thereby form the cover body 23. Examples of means for joining the surface side sheet 20 and the back side sheet 30 include application of an adhesive agent and adhesion by an emboss process, and such means may be used solitarily or in combination. If an emboss process is to be performed, the surface side sheet 20 and the back side sheet 30 may be joined by heat sealing. The parts at which the surface side sheet 20 and the back face side sheet 30 are joined does not have to be water dispersibile, and with the interlabial pad 10 of the present embodiment, the parts at which the surface side sheet 20 and the back face side sheet 30 are joined are not set to become separated by the actions of water. However, it is preferable that the surface side sheet 20 and the back face side sheet 30 are joined in a quasi-manner by an engaging pattern, since the surface side sheet 20 and the back face side sheet 30 will then separate readily after the interlabial pad 10 is discarded into a toilet.

For the surface side sheet 20, a material that is liquid permeable and is not skin-irritating is used. A nonwoven fabric, obtained by a manufacturing method, such as melt blowing, spun bonding, through air method, point bonding, needle punching, wet forming spun lacing, etc., may be cited as such a material. A nonwoven fabric, using pulp, cotton, rayon, acetate, or a biodegradable resin, such as polylactic acid, polybutylene succinate, etc., is especially preferable.

For the back face side sheet 30, a biodegradable or water disintegrable sheet that is liquid impermeable is used. A sheet formed mainly of a water disintegrable polymer, such as polyvinyl alcohol (PVA), alkyl cellulose, etc., may be cited as an example of a water disintegrable sheet. PVA films, film sheets which is provided by modifying a PVA sheet being subject to water repellent treatment by silicon etc. at one side or both sides or partially, PVA films having silicon mixed in, starch films, and films using a biodegradable resin such as polylactic acid, polybutylene succinate, etc. as the raw material, may be cited as examples of a biodegradable sheet.

Also, the surface (referred to hereinafter as "outer surface") 30s of the back side sheet 30, which is positioned at the side opposite to the absorbent body attached preferably has the property of being wetted by water (hereinafter referred to as "water wettability"). An interlabial pad that uses a back face side sheet with water wettability prevents the leakage of body fluids during use and yet becomes wetted with water readily and does not float readily to the water surface when discarded in a toilet.

Examples of the back face side sheet 30, with which the outer surface 30s has water wettability, include sheets which is formed by adhering hydrophilic fibers to one side of a biodegradable or a water disintegrable sheet, laminated paper which is formed by laminating liquid impermeable resin onto one side of a hydrophilic nonwoven fabric using hydrophilic fibers as the raw material, and sheets which is formed by a hydrophilic nonwoven fabric being subject to a water repellent treatment using a sizing agent, etc. so that the water repellency is adjusted by the mixing ratio, etc. Also if necessary, coloring may be applied by mixing an inorganic pigment in a range of 0.1 to 5%. A wet forming spun laced nonwoven fabric may be cited as a specific example of a hydrophilic nonwoven fabric, which is formed with predetermined amounts of fibers having a fiber length in the range of 1 to 38 mm preferably 2 to 20 mm and fineness in the range of 1.1 to 3.3 dtex, like rayon fibers, acetate rayon fibers, cotton fibers, pulp fibers, or synthetic fibers, mixed and adjusted so that the hydrophilic nonwoven fabric has the specific weight is in the range of 10 to 60 g/m$^2$. The liquid impermeable film to be adhered onto the hydrophilic nonwoven fabric preferably has a specific weight of 10 to 40 g/m$^2$ and is adhered by an emboss process or by a water disintegrable adhesive agent at an adhesion percentage in the range of 1 to 30%. A resin to be laminated preferably has a thickness in the range of 10 to 40 µm.

As the absorbent body 40, any absorbent body may be used without restriction as long as body fluids can be absorbed and held. As absorbent body, a highly water-absorbing absorbent body, which is high in liquid absorbing property and can absorb and hold, for example, approximately 15 to 100 times its own weight of liquid, is preferably used. It is furthermore preferable to use an absorbent body that is bulky, is not deformed readily, and is low in chemical irritability. As constituent materials of the absorbent body 40, a pulp, chemical pulp, rayon, acetate., natural cotton, super absorbent polymer, super absorbent polymer fibers, or synthetic fibers may be used solitarily or in blended form. Carboxymethylcellulose (CMC), which is biodegradable, is especially preferable. The form of the absorbent body 40 is not limited in particular and may be sheet-like or powder-like.

The back face side sheet of the interlabial pad of the present invention has parting zone for separation of the back face side sheet into a plurality of small sheet pieces by the actions of water. With the present embodiment, back face side sheet 30 of FIG. 1 is arranged from two small sheet pieces 30a and 30b as shown in FIG. 2 and a longitudinal seam part 90, extending along the longitudinal central line m at which small sheet pieces 30a and 30b overlap so as to cross longitudinal central line m, is the parting zone. The small sheet pieces 30a and 30b overlap with each other over a range of 1 to 25 mm and preferably 5 to 15 mm to form longitudinal seam part 90. When the width of the region from end part 300a of small sheet piece 30a to end part 300b of small sheet part 30b, at which the two small sheet pieces overlap, is less than 1 mm, the small sheet pieces 30a and 30b may separate due to movements of a user and gaps may thus form to cause leakage of body fluids. On the other hand, if this width is greater than 25 mm, it becomes difficult for the small sheet pieces to disperse upon discarding into a toilet. The interlabial pad 10 may therefore become readily retained on a filter element of a small-scale combined treatment septic tank or an aeration tube of an independent treatment septic tank and damage the functions of the septic tank. Furthermore, by the part at which the small sheet pieces 30*a* and 30*b* overlap being excessive, a user may be subject to a foreign-body sensation during use.

In order to prevent clogging of a septic tank, each of the small sheet pieces 30*a* and 30*b* has a size of no more than 60×60 mm, preferably no more than 45×45 mm, and more preferably no more than 30×30 mm as the longitudinal dimension×lateral dimension. The total area of the small sheet pieces 30*a* and 30*b* that make up the back face side sheet 30 may be made slightly greater than the area of the surface side sheet 20. By doing so, leakage of body fluids due to separation of the small sheet pieces 30*a* and 30*b* during the use of the interlabial pad 10 can be prevented. Though the back face side sheet 30 in the present embodiment is formed of two small sheet pieces, it may be formed of a larger number of small sheet pieces, and in this case, the size of a single small sheet piece can be made smaller within the abovementioned range.

The outer surface 30*s* of the back face side sheet 30 is preferably made uneven. The outer surface 30*s* may be made uneven by an emboss process, and the unevenness may also be formed by adhering a nonwoven fabric to the outer surface 30*s* and confounding the fibers of the fabric. When the outer surface 30*s* is made uneven, after the interlabial pad is discarded into a toilet, water will enter readily between the mutually opposing parts of the back face side sheet 30 that is folded in two during use. In particular, in the case where a nonwoven fabric is adhered onto the outer surface 30*s* and a hydrophilic nonwoven fabric is used, the water of the toilet will be absorbed rapidly upon discarding into a toilet. Water will thus enter between the small sheet pieces 30*a* and 30*b* that overlap at the longitudinal seam part 90 and the back face side sheet 30 will disintegrate readily along the longitudinal seam part 90 and become dispersed as the plurality of small sheet pieces.

In order to facilitate the dispersal of the back face side sheet 30 of a used interlabial pad 10 that is discarded into a toilet, in addition to making the outer surface 30*s* uneven, perforation-like slits may be formed in the small sheet piece 30*a*, which is positioned at the side (hereinafter referred to as the "outer side") opposite to the absorbent body side at the longitudinal seam part 90. Also, end part 300*a* of the small sheet piece 30*a* may be folded back so that water will enter readily into the longitudinal seam part 90 from the outer side of the interlabial pad 10. Furthermore, in the case where an adhesive agent is applied between the small sheet pieces 30*a* and 30*b*, a part of a small sheet piece (for example, the vicinity of end part 300*a* of small sheet piece 30*a*) may be left free of any adhesive agent.

Also, the absorbent body 40 may be separated along the longitudinal seam part 90 of the back face side sheet 30 or perforation-like slits may be formed in the absorbent body 40 to make the absorbing body 40 integral to small sheet piece 30*a* or 30*b*. By doing so, since weight and surface area of the absorbent body 40 becomes increased by absorption of water, the back face side sheet 30 can be prevented from floating to the surface of the water inside the septic tank even if a buoyancy is occurred by foam that is generated in a septic tank.

The back face side sheet 30 of the interlabial pad 10 of the present embodiment is adhered and joined to the surface side sheet 20 at peripheral edge parts of the absorbent body 40 by an adhesive agent or by fusion and adhesion by an emboss process. Meanwhile, as mentioned above, the small sheet pieces 30*a* and 30*b*, which make up the back face side sheet 30, are completely separable at longitudinal seam part 90, which is water disintegrable. Thus after the interlabial pad 10 is discarded into a toilet, the longitudinal seam part 90 parts and separates the back face side sheet 30 into the smaller small sheet pieces 30*a* and 30*b*, thereby enabling the load placed on a septic tank to be lightened. Furthermore, by the back face side sheet 30 being provided with the plurality of small sheet pieces 30*a* and 30*b*, impacts that arise due to the movements of a wearer of the interlabial pad 10 can be absorbed and the foreign-body sensation during fitting can be lightened.

With respect to the small sheet piece 30*a*, the small sheet piece 30*b* is positioned so as to cover the side closer to the longitudinal central line m and is disposed at the absorbent body 40 side (referred to hereinafter as the "inner side") at the longitudinal seam part 90. Meanwhile, the other small sheet piece 30*a*, which overlaps with the small sheet piece 30*b* at the longitudinal seam part 90, is positioned to the outer side of the small sheet 30*b* and its end part 300*a* is exposed to the outer side at a position away from the longitudinal central line m. Thus as shown in FIG. 3, when the interlabial pad 10 is folded in two at the vicinity of the longitudinal central line m and fitted between labia, the body fluids that move inside absorbent body from longitudinal central line m towards the outer edges of the interlabial pad 10 are prevented from entering into the longitudinal seam part 90 from the open part at the end part 300*b* of the small sheet piece 30*b* or the end part 300*a* of the small sheet piece 30*a* and the leakage of the body fluid can thus be prevented.

The small sheet pieces 30*a* and 30*b* may or may not be adhered at the longitudinal seam part 90 at which they overlap. The small sheet pieces 30*a* and 30*b* may be adhered by the application of an adhesive agent or by an emboss process.

Figure 4:
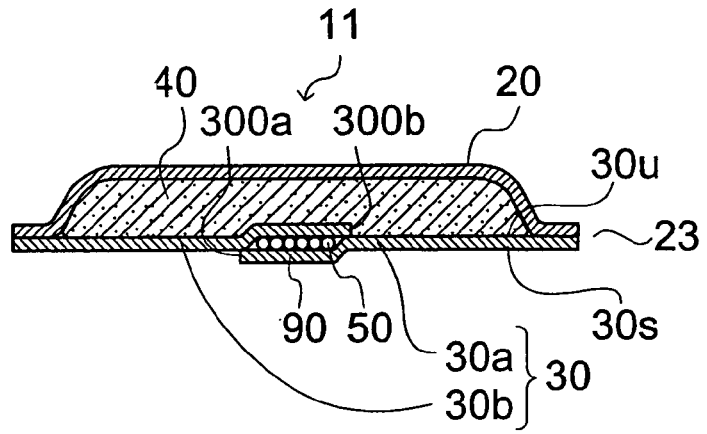
FIG. 4 is a sectional view in the lateral direction of an interlabial pad of a second embodiment of the present invention.

FIG. 4 is a sectional view in the lateral direction of an interlabial pad 11 of a second embodiment of the present invention. A small sheet piece 30*a* and a small sheet piece 30*b* are overlapped at a longitudinal seam part 90 and an adhesive agent 50 is applied between both pieces. The small sheet pieces 30*a* and 30*b* are thereby adhered together, the airtightness is improved, and leakage of body fluids can be prevented. It is sufficient that the adhesive agent 50 be applied to at least one of either small sheet piece 30*a* or small sheet piece 30*b* and the adhesive agent 50 does not have to be applied to one or both of the end part 300*a* of the small sheet piece 30*a* and the end part 300*b* of the small sheet piece 30*b*. Even when the small sheet pieces 30*a* and 30*b* are adhered by an adhesive agent 50 just at the vicinity of the central part in the lateral of the longitudinal seam part 90, body fluids will be prevented from entering readily into the longitudinal seam part 90 as mentioned above and thus the longitudinal seam part 90 will not be lost. Meanwhile, after the interlabial pad 11 is discarded by flushing, water will enter readily into the longitudinal seam part 90 from the outer surface 30*s* of the back face side sheet 30 and the back face side sheet 30 will thus receive the actions of water and separate readily.

Also, the adhesive agent 50 may be applied not just to a part of an absorbent body side surface (referred to hereinafter as the "inner surface") 30*u* of the back face side sheet 30 but to the entirety of this surface. When the adhesive agent 50 is applied to the entire surface of the inner surface 30*u*, the absorbent body 40 can be adhered and fixed to the back face side sheet 30. Also, the chances of end part 300*a* or 300*b* of the small sheet piece 30*a* or 30*b* separating from the other small sheet piece and consequent loss of longitudinal seam part 90 and leakage of body fluids can be reduced.

Adhesive agent 50 is applied to a specific weight in the range of 1 to 20 g/m² and preferably 3 to 10 g/cm². The application pattern of adhesive agent 50 may be a wave-form, O-form, spiral-form, line-form, dotted, etc. and the adhesive agent does not have to be applied to some parts thef longitudinal seam part 90. Since the small sheet pieces 30a and 30b are overlapped at the longitudinal seam part 90, as long as the two small sheet pieces are adhered together at least partially, the leakage of body fluids can be prevented. In the other hand, the back face side sheet 30 can be dispersed readily into the small sheet pieces 30a and 30b when the interlabial pad 11 is discarded into a toilet, and foreign-body sensations during fitting can be lightened.

The type of the adhesive agent 50 can be selected according to the type of the back face side sheet 30. For example, when the back face side sheet 30 is formed of polyvinyl alcohol or other water disintegrable material, a pressure-sensitive adhesive agent or a heat-sensitive adhesive agent of a type, which does not change readily in physical properties even when wetted with water, may be used in a dotted or other intermittent application pattern. This is because the back face side sheet 30 itself is water disintegrable and can be dispersed inside a septic tank even if the adhesive agent 50 is not disintegrated in water. Examples of adhesive agents that are not water disintegrable include pressure-sensitive adhesive agents, having a synthetic rubber, such as styrene-ethylene-butadiene-styrene block copolymer (SEBS), styrene-butadiene-styrene block copolymer (SBS), styrene-isoprene-styrene block copolymer (SIS), etc., as the main component, and heat-sensitive adhesive agents, having a synthetic rubber, such as ethylene-vinyl-acetate copolymer (EVA), etc., as the main component.

Also, as examples of the adhesive agent 50 besides those mentioned above, water-sensitive adhesive agents of a type that is readily changed in physical properties by water and biodegradable agents of a type that is not readily changed in physical properties by water may be cited. When a water-sensitive adhesive agent or a biodegradable adhesive agent is used, the back face side sheet 30 may be formed of either a water disintegrable material or a biodegradable material. The application pattern of the adhesive agent 50 is also not restricted. Specific examples of water-sensitive adhesive agents include polyvinyl alcohols, carboxymethylcellulose, gelatin, and other water-soluble polymers, and polyvinyl acetates, sodium polyacrylates, and other water-swelling polymers. Starch, sodium alginate, guar gum, gellan gum, etc. may be cited as biodegradable adhesive agents. These may also be cross-linked and made into a gel.

Figure 5A:
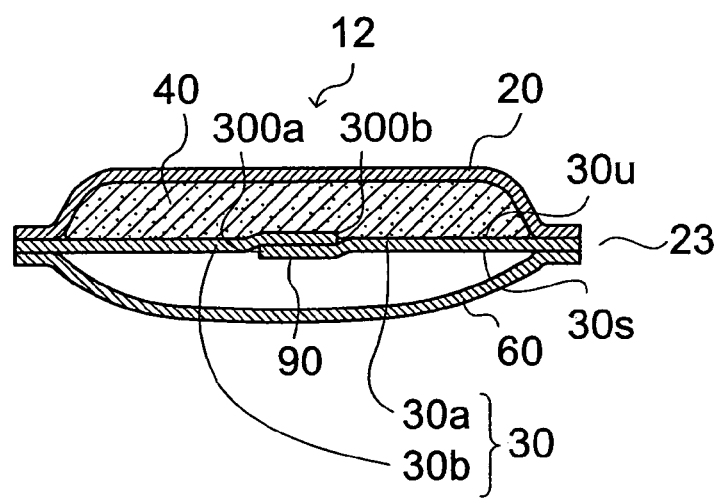
FIG. 5A is a sectional view in the lateral direction of an interlabial pad of a third embodiment of the present invention.
Figure 5B:
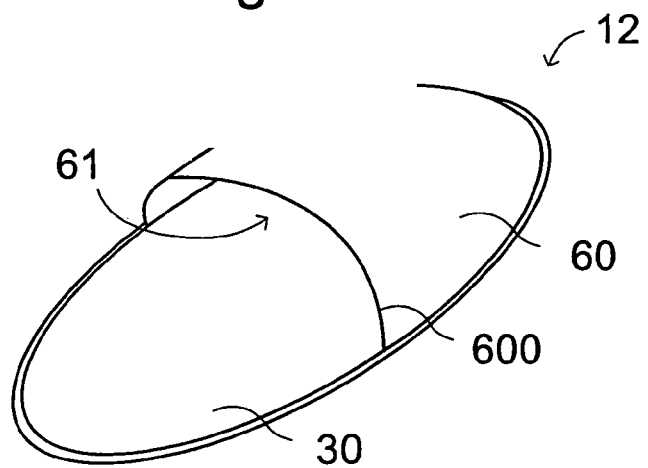
FIG. 5B is a perspective view of the interlabial pad of the third embodiment.

FIG. 5A and FIG. 5B show diagrams of an interlabial pad 12 of a third embodiment of the present invention that has a mini-sheet piece. FIG. 5A is a sectional. schematic view in the lateral direction of the interlabial pad 12. FIG. 5B is a perspective view of the abovementioned interlabial pad 12, placed with a back face side sheet 30 facing upwards so that the left side of the FIGURE becomes the ventral side and the right side becomes the dorsal side when the interlabial pad 12 is fitted on. The back face side sheet 30 of the interlabial pad 12 is equipped with a mini-sheet piece 60. The mini-sheet piece 60 is so as to cover a part of the outer surface 30s of the back face side sheet 30 that is set at the dorsal side when the interlabial pad 12 is worn, and is adhered to the back face side sheet 30 at peripheral edge parts of the interlabial pad 12. A straight end part 600 of the mini-sheet 60 is not adhered to the back face side sheet 30 and a pocket 61, into which a finger is inserted when the interlabial pad 12 is worn and took off, is formed between the mini-sheet piece 60 and the back face side sheet 30.

For the mini-sheet piece 60, a film or a nonwoven fabric such as a spun bonded nonwoven fabric, or a melt blown nonwoven fabric, etc., which has polylactic acid, polybutylene succinate, or other biodegradable material as the raw material, a film or a nonwoven fabric having PVA, CMC, or other water disintegrable material as the raw material, a water disintegrable tissue or spun laced nonwoven fabric, etc. having cellulose fibers or regenerated cellulose fibers, etc. as the main component, etc. may be used. Among these, a spun bonded nonwoven fabric or melt blown nonwoven fabric, which is mainly formed of biodegradable material and is a sheet that has been adjusted to a thickness in a range of 0.1 to 3.3 dtex and a specific weight in a range of 15 to 40 g/m² and has been subject to a mechanical corrugating process, is favorable.

Figure 6:
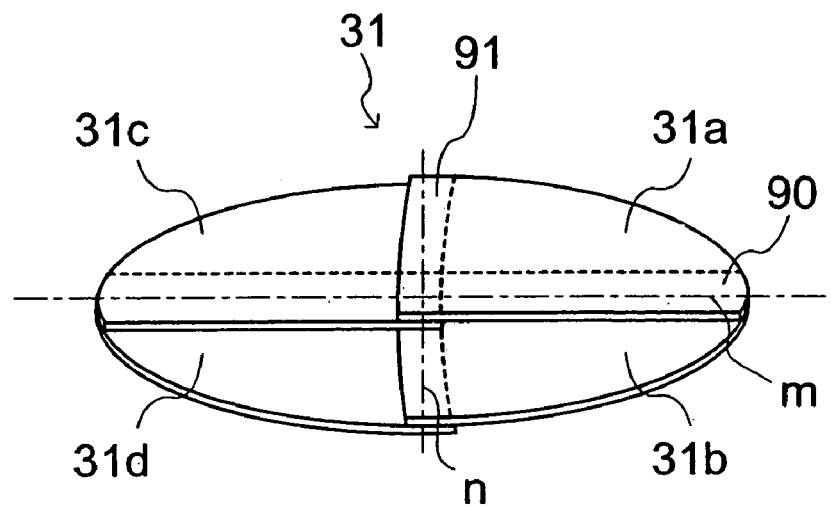
FIG. 6 is a perspective view showing a back face side sheet of an interlabial pad of a fourth embodiment of the present invention.

A back face side sheet 31 of an interlabial pad of a fourth embodiment of the present invention shall now be described using FIG. 6. FIG. 6 is a perspective view showing the back face side sheet 31 of this embodiment, placed so that the left side of the FIGURE becomes the ventral side when the interlabial pad is worn and so that the side at which the absorbent body is disposed is the upper side. The back face side sheet 31 is provided with four small sheet pieces 31a, 31b, 31c, and 31d. As with the interlabial pad 10 of the first embodiment of FIG. 1, a longitudinal seam part 90 is provided near a longitudinal central line m. Also in the present embodiment, a lateral seam part 91 is provided near a lateral central line n. The small sheet piece 31a is overlapped with the small sheet piece 31b at the longitudinal seam part 90 and with the small sheet piece 31c at the lateral seam part 91, in both cases so that the small sheet piece 31a is positioned at the side at which the absorbent body is disposed, in other words, at the inner side. The small sheet piece 31d is overlapped with the small sheet piece 31c at the longitudinal seam part. 90 and with the small sheet piece 31b at the lateral seam part 91, in both cases so that the small sheet piece 31d is positioned at the inner side. The width of mutual overlap of the small sheet pieces at the seam parts 90 and 91 is 1 to 25 mm and preferably 5 to 15 mm.

With this embodiment, the small sheet pieces 31c and 31d, which cover the side that becomes the ventral side when the interlabial pad is fitted on (left side of FIG. 6), are overlapped with the small sheet piece 31a and the small sheet piece 31b at the lateral seam part 96 so as to be at the outer side. Body fluids that flow in the direction from the dorsal side to the ventral side of the interlabial pad (from the left to right direction in FIG. 6) are thus prevented from entering between the small sheet pieces 31a and 31c or between the small sheet pieces 31b and 31c from the gaps of the lateral seam part 91, and the leakage of body fluids can thus be prevented. Also, in the case where the back face side sheet 31 is provided with a mini-sheet piece, having an opening for insertion of a finger in the direction from the ventral side to the dorsal side, the finger can be prevented from catching on to the lateral seam part 91 and can thus be prevented from damaging the lateral seam part 91 and giving rise to a cause of body fluid leakage.

Figure 7:
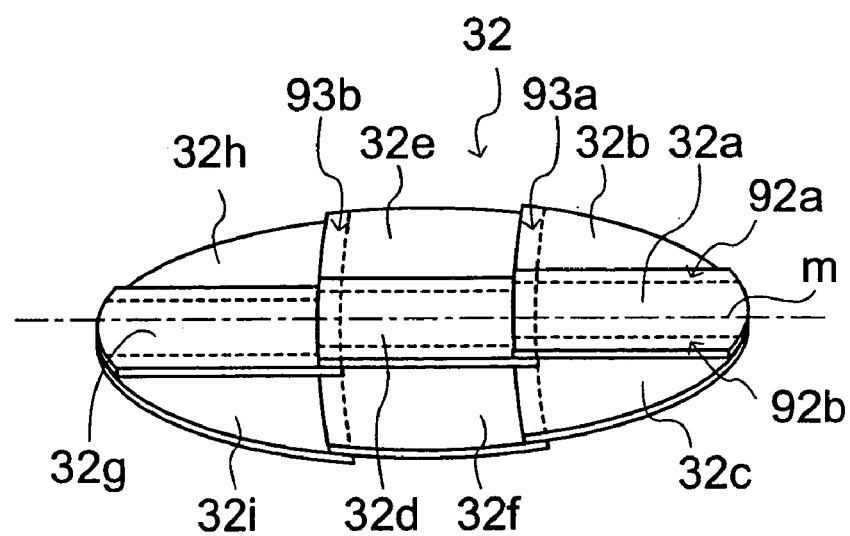
FIG. 7 is a perspective view showing a back face side sheet of an interlabial pad of a fifth embodiment of the present invention.
Figure 8:
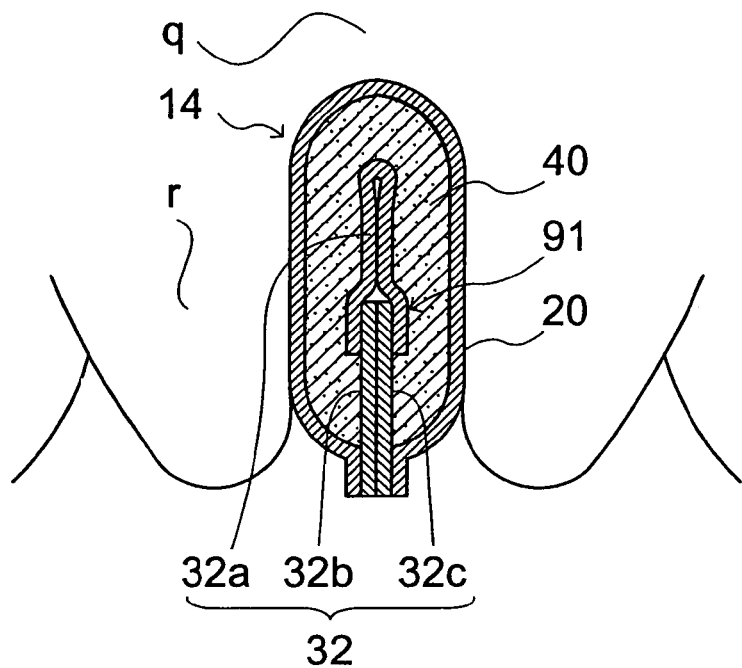
FIG. 8 is a diagram showing a state in which the interlabial pad of the fifth embodiment is fitted between labia.

FIG. 7 is a plan view showing a back face side sheet 32 of an interlabial pad 14 of a fifth embodiment of the present invention, placed so that the part that becomes the ventral side is positioned at the left side when the interlabial pad is fitted on and so that the side at which the absorbent body is disposed faces upwards. FIG. 8 is a diagram showing a state in which the abovementioned interlabial pad 14 is fitted between. labia. In FIG. 8, the interlabial pad 14 is folded in two along a longitudinal central line m and is fitted between labia. The back face side sheet 32 of the interlabial pad 14 is arranged from nine small sheet pieces 32a, 32b, 32c, 32d, 32e, 32f, 32g, 32h, and 32i.

With the present embodiment, a longitudinal seam part 92 has a first longitudinal seam part 92a and a second longitudinal seam part 92b, and a lateral seam part 93 has a first lateral seam part 93a and a second lateral seam part 93b. With the small sheet pieces that mutually overlap at the longitudinal seam part 92, the small sheet pieces (32a, 32d, and 32g), which cover the side closer to a longitudinal central line m, are overlapped with the small sheet pieces (32b, 32e, 32h, 32c, 32f, and 32i), which cover the side closer to the peripheral parts, so as to be at the outer side. With the back face side sheet 32, since the longitudinal seam part 92 is not set at the vicinity of the vestibular floor when the interlabial pad 14 is fitted on as shown in FIG. 8, the foreign-object sensation during fitting can be lightened.

Also, with the small sheet pieces that mutually overlap at lateral seam part 93, the small sheet pieces (for example, 32h, 32g, and 32i), which cover the side closer to the side that is to become the ventral side (left side of the FIG. 7) when the interlabial pad is fitted on, are overlapped with the small sheet pieces (for example, 32e, 32d, and 32f), which cover the side closer to the side that is to become the dorsal side (right side of the FIG. 7.), so as to be at the outer side. Thus body fluids, which are discharged from the ostium vaginae positioned near the small sheet piece 32a, and flows in the direction of the ventral side at the left side of FIG. 7, are prevented from entering between overlapping the small sheet pieces from the gaps of the seam parts 92 and 93 and the leakage of body fluids can thus be prevented. Furthermore, in the case where the back face side sheet 32 is provided with a mini-sheet piece, having an opening for insertion of a finger in the direction from the ventral side to the dorsal side, the finger can be prevented from catching on to the lateral seam part 93 and can thus be prevented from damaging the lateral seam part 93 and giving rise to a cause of body fluid leakage.

Figure 9:
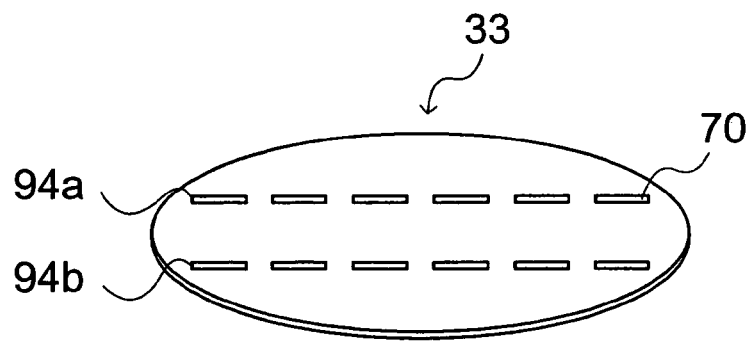
FIG. 9 is a perspective view showing a back face side sheet of an interlabial pad of a sixth embodiment of the present invention.

The back face side sheet may also be arranged from a single sheet piece. FIG. 9 is a perspective view showing a back face side sheet 33 of an interlabial pad of a sixth embodiment of the present invention as viewed from the outer side, that is, as viewed with the side opposite to the absorbent body side facing upward. With this embodiment, the back face side sheet 33 has two parting lines 94a and 94b and is provided with a single sheet piece. Parting lines 94a and 94b are parts at which slits 70, provided in the back face side sheet 33, are aligned serially along the longitudinal directon.

The slits 70 have a length of 10 mm each and are disposed discontinuously at a pitch of a 5 mm interval. Since these parts are voids formed by slits 70, they are weak in physical strength and thus cause the back face side sheet 33 to disintegrate and disperse when the interlabial pad is flushed down a toilet. With the back face side sheet 33 of FIG. 9, due to the gaps that the slits 7 form, a small amount of body fluids may permeate from these parts. In order to prevent this, a part of the back face side sheet may be overlapped to cover the gaps.

Figure 10:
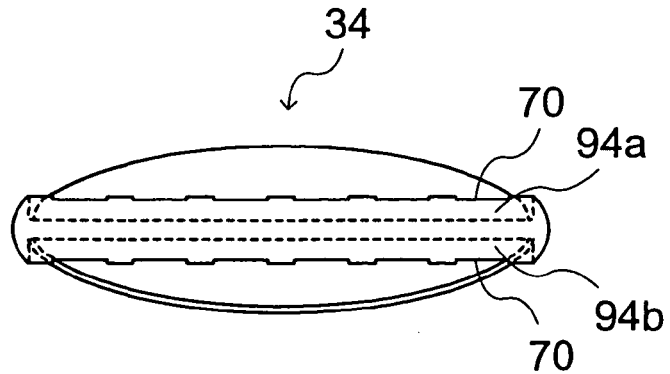
FIG. 10 is a perspective view showing a back face side sheet of an interlabial pad of a seventh embodiment of the present invention.

FIG. 10 is a perspective view showing a back face side sheet 34 of an interlabial pad of a seventh embodiment of the present invention as viewed from the outer side, that is, as viewed with the side opposite to the absorbent body side facing upward. With the seventh embodiment, a part of the back face side sheet 34, having parting lines 94a and 94b formed by slits 70, is overlapped so as to cover the gaps that the slits 70 form. With this embodiment, due to the gaps of the slits 70 being covered with the back face side sheet 34 folded, the leakage of body fluids can be prevented. Also as with the above-described back face side sheet 33 of the sixth embodiment, the back face side sheet 34 disintegrates near the slits 70 and disperses into small pieces upon being flushed down a toilet.

Next, an individual packaging body of interlabial pad, in which an interlabial pad covered with a packaging sheet is contained, shall be described.

Figure 11A:
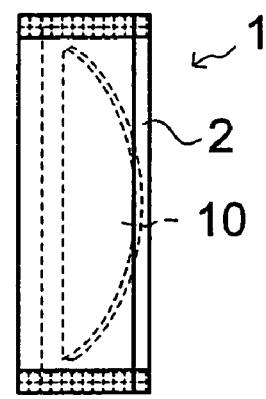
FIG. 11A is a plan view of a packaging body for individual package of interlabial pad according to the present invention.
Figure 11B:
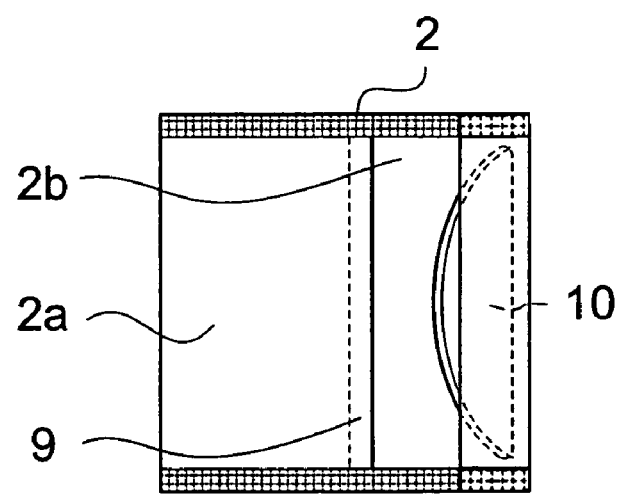
FIG. 11B is a plan view of a state in which the packaging body for individual package of FIG. 11A is partially opened up.

FIG. 11A is a plan view of a packaging body 1 according to the present invention, and FIG. 11B is a plan view of a state in which the packaging body 1 of FIG. 11A is partially opened up. As shown in FIG. 11A, the packaging body 1 has an interlabial pad 10, which was shown in FIG. 1A, and a packaging sheet 2, which covers the interlabial pad 10. As shown in FIG. 11B, the packaging sheet 2 is arranged from two short sheet pieces 2a and 2b, and these small sheet pieces overlap to form a seam part 9.

The packaging sheet 2 may be a liquid permeable sheet, which is used for the surface side sheet 20 of the abovementioned the interlabial pad 10, or may be a liquid impermeable sheet, which is used for the back face side sheet 30. However, in order to prevent soiling the interlabial pad 10 when the individual packaging body 1 is erroneously dropped or soiled with water, etc. while carrying, it is preferable to use a liquid impermeable sheet as the packaging sheet 2.

Though the size of the packaging sheet 2 depends on the shape of the interlabial pad 10, which is enclosed in the individual packaging body, it must be made at least larger than the interlabial pad 10, because it must cover the entirety of interlabial pad 10. Specifically, when the packaging sheet 2 is made to have a rectangular shape as shown in FIG. 11B, it preferably has a size in the range of 40 to 360 mm in the longitudinal direction and 25 to 200 mm in the lateral direction in the opened-up state. Also in consideration of the load placed on a septic tank, each of the small sheet pieces 2a and 2b, which make up the packaging sheet 2, has a longitudinal dimension×width dimension of no more than 60×60 mm, preferably no more than 45×45 mm, and more preferably no more than 30×30 mm.

The range in which the small sheet pieces 2a and 2b overlap is 1 to 2 mm and preferably 5 to 15 mm, and preferably small sheet pieces 2a and 2b are adhered together by application of an adhesive agent to one or both of the small sheet pieces. As the adhesive agent to be used for adhering together the small sheet pieces, the same adhesive agent used for adhering together the small sheet pieces that make up a back face side sheet of an interlabial pad may be used. The adhesive agent is applied to a specific weight in the range of 1 to 20 g/m² and preferably 3 to 10 g/cm², and the application pattern may be selected suitably from among wave-form, O-form, spiral-form, line-form, dotted, solid, etc.

Also, so that water will be absorbed rapidly in a toilet and the seam part 9 will disintegrate readily when the packaging sheet 2 is discarded into the toilet after use, a hydrophilic nonwoven fabric may be disposed so as to sandwich a liquid-impermeable packaging sheet.

EXAMPLES

The water disintegrability of the present invention's interlabial pad shall now be described based on examples.

Figure 12A:
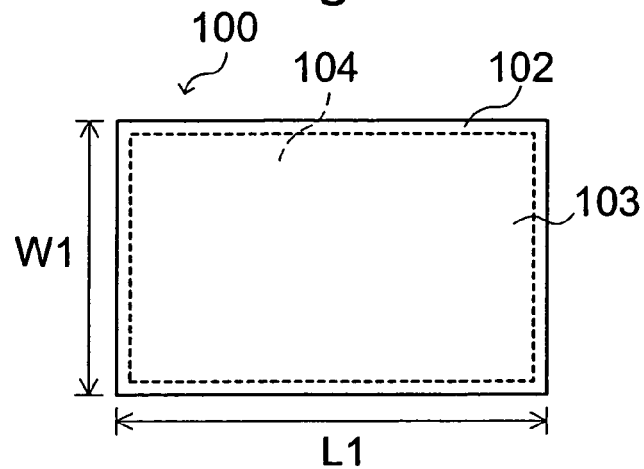
FIG. 12A is a plan view of an interlabial pad used for evaluating the water disintegrability.
Figure 12B:
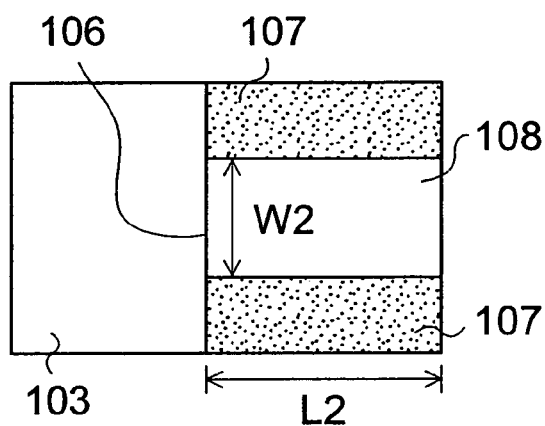
FIG. 12B is a bottom view of the interlabial pad.
Figure 12C:
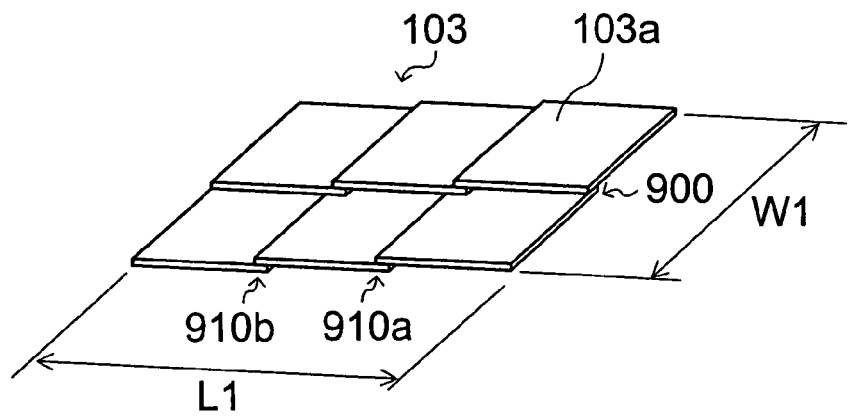
FIG. 12C is a perspective view of a back face side sheet of the interlabial pad.

FIG. 12A is a plan view of an interlabial pad 100 used for evaluating the water disintegrability, FIG. 12B is a bottom view of the interlabial pad 100, and FIG. 12C is a perspective view of a back face side sheet 103 of the interlabial pad 100 of FIG. 12A.

As shown in FIG. 12A, the interlabial pad of this example is equipped with a surface side sheet 102 and a back face side sheet 103, which make up a cover body, an absorbent body 104, enclosed in these sheets, and a mini-sheet piece 105. The surface side sheet 102 is a wet forming spun lace, prepared by mixing rayon fibers, with a fiber length of 5 mm and fineness of 1.7 dtex, and conifer Kraft pulp at proportions of 70% and 30%, respectively, subjecting the fibers to a papermaking process, and then forming into a sheet by hydro-entanglement. The absorbent body 104 is prepared by making a conifer pulp sheet into a cotton-like pulp by means of a pulp crusher, adjusting the specific weight of the pulp to 300 g/m$^2$, adjusting the thickness to 4 mm by a press, and forming into a rectangular shape with a width of 52 mm and 85 mm. The back face side sheet 103 is arranged from six small sheet pieces 103a of laminated nonwoven fabric, prepared by laminating a polybutylene succinate resin to a thickness of 20 μm onto a water dispersible paper with dimensions of 37×34 mm and a specific weight of 18 g/m$^2$. As shown in FIG. 12C, with the six small sheet pieces 103a, adjacent small sheet pieces are overlapped with each other at a longitudinal seam part 900, having a width of 10 mm, and at a lateral seam parts 910a and 910b, having a width of 10 mm each and being disposed at positions that divide the longitudinal direction into three substantially equal parts. Between the small sheet pieces 103a, which overlap at the longitudinal seam part 900 and the lateral seam parts 910, a heat-sensitive, water disintegrable adhesive agent, having polyvinyl acetate as the main component, is applied at an application amount of approximately 5 g/m$^2$ in a dotted application pattern and the small sheet pieces 103a are thereby adhered to each other.

Also, over the entire surface of the back side face sheet 103 at the side at which absorbent body 104 is disposed, a plurality of lines of a water disintegrable adhesive agent, having polyvinyl alcohol as the main component, are applied in a continuous, spiral form at an application amount of 3 g/m$^2$ specific weight. After application of the adhesive agent, the absorbent body 104 is positioned at the absorbent body side of the back face side sheet 103. Then at the surface of one side of the absorbent body 104, that is, the surface at the side opposite to the side at which the back face side sheet 103 is disposed, the surface side sheet 102 is positioned and an engagement emboss process of a lattice form of 2 mm width is performed along the peripheral edges of absorbent body 104, and the surface side sheet 102 and the back face side sheet 103 are joined form the cover body with the absorbent body 104 being positioned between the surface side sheet 102 and the back face side sheet 103.

The mini-sheet piece 106, formed of a water dispersible paper with a specific weight of 18 g/m$^2$, is positioned at the surface of the back face side sheet 103 at the side opposite to the absorbent body side so as to cover one side of the longitudinal end part of the interlabial pad 100. The mini-sheet piece 106 covers the back face side sheet 103 over a range such that length L2 will be 50 mm. At the end parts of the mini-sheet piece 106 that are parallel to the longitudinal direction, a water disintegrable adhesive agent, having polyvinyl acetate as the main component, is applied to form joined parts 107. An opening 108, by which a finger can be inserted between the back face side sheet 103 and the mini-sheet piece 106 is thus formed. Also, the width of application of the adhesive agent to be applied to both side parts of the mini-sheet piece 106 is set so that the opening width W2 of the opening 106 will be 25 mm.

Thereafter, the interlabial pad 100 is cut at positions 3 mm from the peripheral edges of the absorbent body 104 so that the value of maximum width W1 will be 58 mm and the value of maximum length L1 will be 91 mm.

Also, as a comparative example for the above-described example, five test pieces each of PG Corp.'s interlabial pad named Envive (Moderate) were discarded by flushing down simulated flush toilets and the water disintegration states of the example and the comparative example were observed visually.

In the tests, simulated night soil treatment devices, each having a flush toilet and septic tank, were used. FIG. 13 are explanatory diagrams for describing the simulated night soil treatment devices, with FIG. 13A showing a device with a small-scale combined treatment septic tank and FIG. 13B showing a device with an independent treatment septic tank.

The simulated night soil treatment device 200 of FIG. 13A is provided with a semi-siphon type Western-style toilet 201 and a small-scale combined treatment septic tank 203 and with this device, the discharge amount is 8 liters per single time of flushing and the diameter of the trap part is 53 mm. The toilet 201 and the small-scale combined treatment septic tank 203 are connected by a pipe 202, and the pipe 202 is set to have a diameter of 100 mm, a slope grade of ¹⁄₁₀₀, and a length L3 of 10 m. The small-scale combined treatment septic tank 203 has a filter element 203a. Meanwhile, a simulated night soil treatment device 203 of FIG. 13B has, in place of the small-scale combined treatment septic tank 203 of FIG. 13A, an independent treatment septic tank 204, having an aeration tube 204a. The interiors of the septic tanks 203 and 204 were both filled with tap water. As the filter element 203a of the small-scale combined treatment septic tank 203, skeletal spheres of a diameter of 150 mm, which are used in model CXIII of AMS Co., Ltd., are filled inside the small-scale combined treatment septic tank 203 to a height of approximately 650 mm. Also, the aeration tube 204a of the independent treatment septic tank 204 is made to have a diameter of 18 mm.

When the interlabial pad 100 was discarded by flushing down the above-described toilet 201, the interlabial pad 100 flowed through the pipe 202, and by the time the interlabial pad 100 was reached to the septic tank 203 or 204, the back face side sheet 103 was dispersed into the plurality of small sheet pieces 103a, neither clogging the filter element 203a of the small-scale combination treatment tank 203 nor being entangled onto the aeration tube 204a of the independent treatment septic tank 204. On the other hand, with the interlabial pad of the comparative example, it was visually observed that the back face side sheet clogged the filter element 203a of the small-scale combination treatment tank 203 and became entangled onto the aeration tube 204a of the independent treatment septic tank 204.

It was thus confirmed that by providing water disintegrable parting lines in the back face side sheet, the functions of a septic tank will not be damaged when the interlabial pad is discarded by flushing down a toilet.

Though the interlabial pad 100 of the present invention was described above, the present invention is inherently not limited to the illustrated examples and various modifications may be added within a scope that suits the gist of the invention described above and all such modifications are included within the scope of the art of the present invention.

With the present invention, a back face side sheet is arranged by providing a plurality of mutually adjacent small sheet pieces so that they overlap with each other. Thus when discarded in a toilet after use, the back face side sheet disperses into the plurality of small sheet pieces upon coming in contact with water and the damaging of the functions of a septic tank by the respective small sheet pieces is thereby lessened.

Also, of the small sheet pieces that are overlapped at a longitudinal seam part, the small sheet pieces, which cover the side closer to a longitudinal central line, are disposed at the side at which an absorbent body is positioned. Thus in a state in which an interlabial pad is folded along the longitudinal central line and fitted between labia, the end parts of the small sheet pieces, which, among the small sheet pieces that are overlapped at the longitudinal seam part provided in the back face side sheet, are positioned at the side at which the absorbent body is positioned, are not directed in the direction of stopping the body fluids that flow from the longitudinal central line towards the peripheral edges of the interlabial pad and thus the body fluids will not leak while the interlabial pad is fitted on.

Also, by making the side of the back face side sheet that is opposite to the body side uneven, even when the interlabial pad is discarded in a toilet in the folded state after use, water will enter readily from the gaps between the mutually facing uneven parts of the folded back face side sheet. The folded interlabial pad will thus open instantaneously in water, the back face side sheet will come in contact uniformly with water from the surface of the back face side sheet, and water will enter readily into the seam parts.

Also, since the packaging sheet of the individual packaging body that encloses the interlabial pad is arranged from a plurality of small sheet pieces and is thus dispersed readily into the plurality of small sheet pieces when discarded into a toilet after use, the damaging of the functions of a septic tank is lightened. Also, since the entry of water (moisture) from the exterior can be shut out without fail, the sanitary state of the enclosed interlabial pad can be maintained.

What is claimed is:

1. An interlabial pad comprising:
   an absorbent body for absorbing liquid;
   a surface side sheet having a permeable property for liquids, being configured for contacting a body, and covering a first face side of the absorbent body;
   a back face side sheet formed by a plurality of sheet pieces that contact a second face side of the absorbent body opposite to the first face side;
   a junction joining the surface side sheet and the back face side sheet at a peripheral edge of the absorbent body, the absorbent body being enclosed thereby between the surface side sheet and the back face side sheet;
   a mini-sheet piece formed of either a water disintegrable material or a biodegradable material, the mini-sheet piece being adhered to the back face side sheet at the junction joining the surface side sheet and the back face side sheet, forming a pocket between the mini-sheet piece and the back face side sheet, wherein a finger of a user may be inserted into the pocket; and
   one or more seam parts that are either water disintegratable or biodegradable, the one or more seam parts extending from 5 to 15 mm between edges of overlapping portions of the plurality of sheet pieces, wherein:
   pairs of the plurality of sheet pieces are only partially overlapping at the overlapping portions,
   at least one of the one or more seam parts comprises a longitudinal seam part extending linearly along a longitudinal central line of the interlabial pad between longitudinal ends of the absorbent body, and
   the one or more seam parts extend from 5 to 15 mm between edges of the overlapping portions of the plurality of sheet pieces.

2. The interlabial pad according to claim 1,
   wherein another one of the one or more seam parts comprise a lateral seam part extending in a lateral direction and crossing over the longitudinal seam part of the interlabial pad.

3. A packaging body for individually packaging an interlabial pad, comprising:
   a packaging sheet; and
   an interlabial pad according to claim 1;
   wherein the interlabial pad is covered by the packaging sheet; and
   wherein the packaging sheet is provided with a continuous or discontinuous parting zone that is parted by actions of water, along which the packaging sheet is separated into a plurality of small sheet pieces after the packaging sheet is discarded in a toilet.

4. The packaging body for individually packaging an interlabial pad according to claim 3;
   wherein the packaging sheet is a liquid impermeable sheet with an impermeable property against liquid.

5. The interlabial pad according to claim 1, further comprising a folded structure in which the back face side sheet is folded face to face on a folding axis along the longitudinal central line,
   wherein an edge of one of the overlapping portions of the plurality of sheet pieces is positioned away from the folding axis.

6. The interlabial pad according to claim 1, wherein each of the one or more seam parts comprises at least one of the following features:
   i) an adhesion with an emboss process;
   ii) an adhesion with a water disintegrable adhesive agent;
   iii) an adhesion with an intermittent application pattern of a pressure-sensitive adhesive agent;
   iv) an adhesion with an intermittent application pattern of a heat-sensitive adhesive agent;
   v) an adhesion with a water-sensitive adhesive agent;
   vi) an adhesion with a biodegradable adhesive agent; or
   vii) a folding back over perforation-like slits formed in the back face side sheet.

7. The interlabial pad according to claim 1, wherein the one or more seam parts further include a first lateral seam part and a second lateral seam part spaced apart from each other along the longitudinal seam part of the back face side sheet sheet, both lateral seam parts extending in a lateral direction and crossing over the longitudinal seam part.

8. The interlabial pad according to claim 1, wherein an outer surface side of the back face side sheet opposite to an inner surface side of the back face side sheet contacting the absorbent body comprises hydrophilic fibers.

9. The interlabial pad according to claim 8, wherein the inner surface side of the back face side sheet is formed by laminating the hydrophilic fibers with liquid impermeable resin.

10. The interlabial pad according to claim 8, wherein the inner surface side of the back face side sheet is formed with a water-repellant treatment.

11. The interlabial pad according to claim 1, wherein the back face side sheet comprises a water-disintegratable polymer.

12. The interlabial pad according to claim 1, wherein the back face side sheet comprises a film including a biodegradable resin.

* * * * *